United States Patent [19]

Blumenthal

[11] Patent Number: 4,840,627
[45] Date of Patent: Jun. 20, 1989

[54] ARTIFICIAL EYE LENS AND METHOD OF TRANSPLANTING SAME

[76] Inventor: Michael Blumenthal, c/o Abrams, 1136 Fifth Ave., New York, N.Y. 10028

[21] Appl. No.: 51,159

[22] Filed: May 13, 1987

Related U.S. Application Data

[63] Continuation of Ser. No. 849,325, Apr. 8, 1986, abandoned.

[51] Int. Cl.⁴ .............................................. A61F 2/16
[52] U.S. Cl. ........................................................ 623/6
[58] Field of Search ............................................. 623/6

[56] References Cited

U.S. PATENT DOCUMENTS

| 4,424,597 | 1/1984 | Schlegel | 623/6 |
| 4,449,257 | 5/1984 | Koeniger | 623/6 |
| 4,573,998 | 3/1986 | Mazzocco | 623/6 |
| 4,588,406 | 5/1986 | Federov et al. | 623/6 |
| 4,673,406 | 6/1987 | Schlegel | 623/6 |

FOREIGN PATENT DOCUMENTS

| WO/85/009-65 | 3/1985 | PCT Int'l Appl. | 623/6 |
| 2151371A | 7/1985 | United Kingdom | 623/6 |

OTHER PUBLICATIONS

Ocular Surgery News (Reprint from Ocular News Surgery), Sep. 1, 1984, vol. 2, No. 17.

Primary Examiner—Ronald L. Frinks
Attorney, Agent, or Firm—Pollock, Vande Sande & Priddy

[57] ABSTRACT

An intraocular lens made of a hydrogel material, preferably having about 60% water content, and defining a central, preferably bi-convex, optical portion and two oppositely situated, integrally formed, elongate, tapered fixation elements and a method for implanting same.

14 Claims, 3 Drawing Sheets

ARTIFICIAL EYE LENS AND METHOD OF TRANSPLANTING SAME

This application is a continuation, of Ser. No. 849,325, filed on Apr. 8, 1986, now abandoned.

FIELD OF THE INVENTION

The present invention relates to artificial lenses for eyes, in general, and to soft intraocular lenses and a method for implanting them in the posterior chamber or anterior chamber, in particular.

BACKGROUND OF THE INVENTION

A number of eye diseases exist wherein it is necessary to surgically remove the natural lens of the eye. During such surgery, it is necessary to replace the lens with an artificial lens, if the patient is to regain the use of the eye. Numerous artificial lenses have been developed and disclosed in the patent literature. These include glass intraocular lenses or hard plastic lenses known as PMMA that are held in place in the eye with loops, clips, staves and sutures.

Lenses for insertion into the lens capsule are illustrated, for example, in U.S. Pat. Nos. 4,251,887, 4,254,510, 4,476,591, 4,477,931. Lenses adapted for attachment to the ciliary body of the eye are disclosed, inter alia, in U.S. Pat. Nos. 4,253,199, 4,249,272, 4,254,509. Still other artificial intraocular lenses are disclosed in U.S. Pat. Nos. 4,253,200, 4,254,511, 4,257,130, 4,480,340, 4,338,687 and 4,414,694. There is shown in U.S. Pat. No. 4,277,852 an intraocular lens with supporting mount which is automatically implantable with correct optical orientation of the correction axis.

These lenses are generally so-called hard lenses which are relatively inflexible. There are also known soft lenses made of a flexible material. Soft lenses require the selection of an appropriate material which is sufficiently flexible yet has the necessary optical qualities, which is non-toxic and which can be manipulated to the desired shape. They also require an effective design to provide a suitable optical region and effective fixation.

U.S. Pat. No. 4,424,597 to Schlegel discloses a posterior chamber implant lens comprising a homogeneous, clear, vulcanized silicone rubber optical portion and a radially outwardly extending, thin-walled support encircling the centerpoint of the lens body and having several openings distributed thereover. The lens of silicone rubber is is flexible and of a constant size since it does not absorb fluid in the eye. Thus, in order to implant this lens, the incision must be as large as the lens, or the lens must be folded for insertion and then unfolded within the eye. Furthermore, this lens is very thin so that upon fibrosis, when the capsule constricts about it, the lens often pops out.

There is shown in U.S. Pat. No. 4,449,257 to Koeniger an intraocular soft lens of HEMA plastic cut into a round lens with concentric grooves around peripheral margins which frictionally engage the rough interior walls of the posterior lens capsule. Koeniger replaces the entire natural lens with an artificial lens of substantially identical shape and size. Due to the absorptive nature of the HEMA plastic material, when implanted, the dry lens softens by absorbing aqueous humor and expands to fill the lens bag. The disadvantages of this method are twofold. First, a relatively large incision is required through which the lens is inserted, due to the width of the lens. Second, since the power of the lens depends on its curvature, the lens of this shape detracts from normal vision because the size and shape of the lens physiologically does not permit the provision of the necessary optical diopters, in the shape described.

There is shown in U.S. Pat. No. 4,253,199 a deformable implant lens including upper and lower pieces which are sealed around the edges thereof leaving a lip or flap on one or both pieces. The flap is attached to the ciliary body as by sutures. Insertion of the lens is accomplished while the implant is partially dehydrated. The point at which the lens pieces are bent to form the lip is a weak point about which the lens which can deform during dehydration, causing difficulty during insertion.

SUMMARY OF THE INVENTION

It is an object of the present invention to provide an intraocular soft lens including a central optical portion and a fixation or support portion which permits easy and accurate implantation in the desired location in the eye, preferably in a partially dehydrated state for expansion during implantation, to give relatively rapid and efficient fixation within the eye.

There is thus provided in accordance with the present invention an intraocular lens made of a hydrogel material, preferably having about 60% water content, and defining a central, preferably bi-convex, optical portion and two oppositely situated, integrally formed, elongate, tapered fixation elements.

According to a preferred embodiment, the lens defines a vertical cross-section which is gradually tapered from the optical portion along the length of the fixation elements, permitting dehydration without substantial deformation.

There is also provided in accordance with the present invention a method of operating in the eye including the steps of removing the lens of the eye and part of the anterior capsule portion, inserting a lens implant of a hydrogel material defining an optical portion and two oppositely situated, integrally formed, elongate, tapered fixation elements in a partially dehydrated state into the posterior chamber of the eye, and permitting the lens implant to expand into fixative contact in a predetermined location.

BRIEF DESCRIPTION OF THE DRAWINGS

The lens of the present invention will be further understood and appreciated from the following detailed description taken in conjunction with the drawings in which.

DETAILED DESCRIPTION OF THE INVENTION

Figure 1:
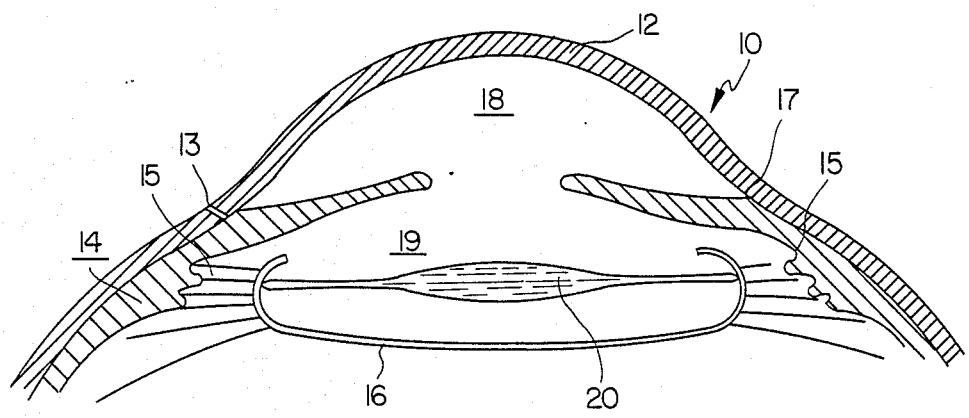
FIG. 1 is a schematic illustration of an eye with a lens according to the present invention inserted into the posterior lens capsule.
Figure 5:
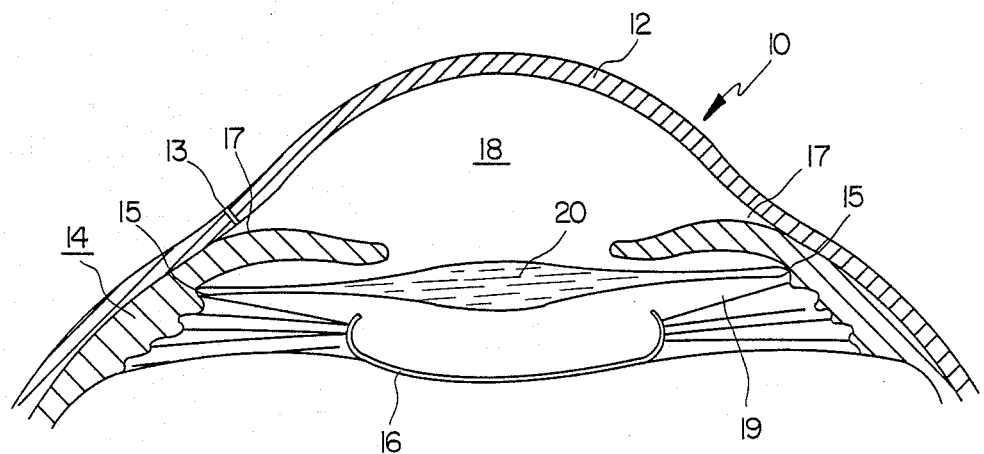
FIG. 5 is a schematic illustration of an eye with a lens according to the present invention inserted into the posterior chamber and affixed to the ciliary sulcus.

With reference to FIG. 1 there is shown a schematic illustration of an eye, generally designated 10, including a cornea 12, limbus 13, ciliary body 14 and lens capsule 16. The ciliary body defines the boundary between the so-called anterior chamber 18 and the posterior chamber 19. An artificial replacement lens implant 20 is illustrated inserted in place in the eye, inserted within the lens capsule. FIG. 5 shows a similar illustration, like elements having like reference numerals, wherein the lens 20 is inserted in the posterior chamber and affixed to the ciliary sulcus 15.

Figure 6:
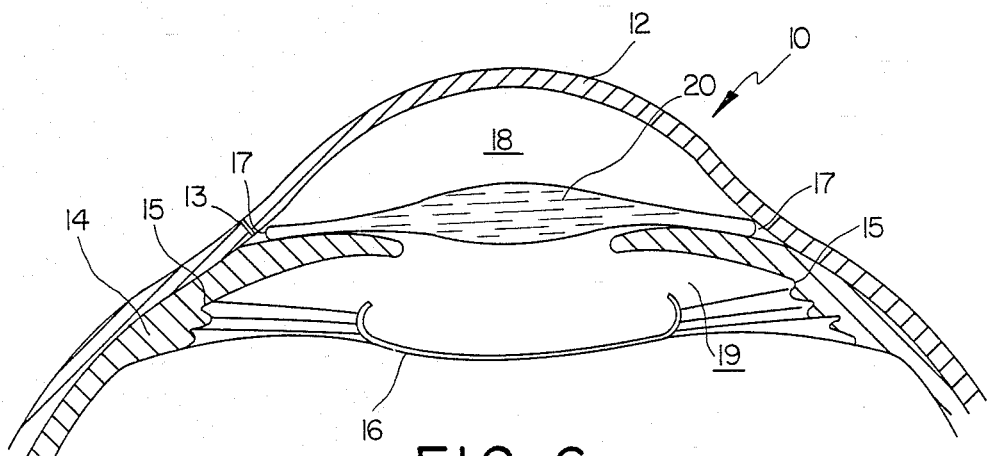
FIG. 6 is a schematic illustration of an eye with a lens according to the present invention inserted into the anterior chamber and affixed in the angle.

During surgery for removal of the natural lens, an incision is made in limbus 13, at least part of the anterior portion of the lens capsule is removed, and the lens and other lens debris is removed by phaco-emulsification or any mechanical action. According to the present invention, a replacement lens of specific design is then introduced and affixed in a predetermined location in the eye, particularly within the lens capsule 16 ("in the bag", as shown in FIG. 1), affixed to the ciliary sulcus 15 (as shown in FIG. 5), or in the anterior chamber angle 17 (as shown in FIG. 6).

Figure 3:
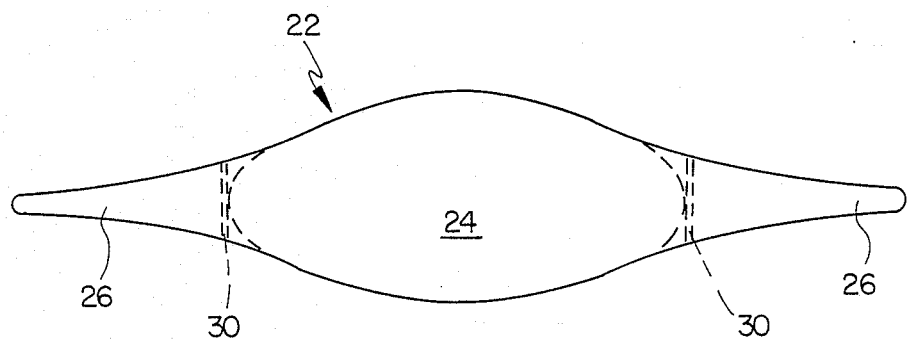
FIG. 3 is a side sectional view of the lens of FIG. 2.
Figure 2:
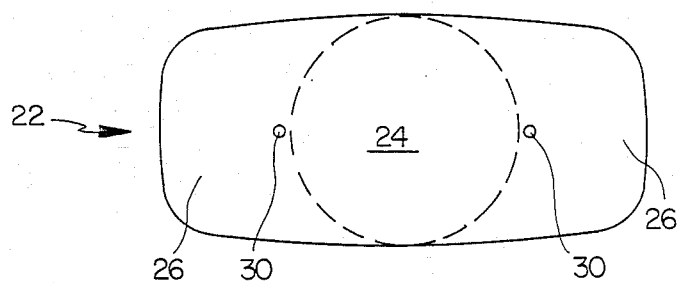
FIG. 2 is a plan view illustration of an intraocular lens constructed and operative in accordance with an embodiment of the present invention.

An intraocular lens 22 constructed in accordance with one embodiment of the present invention is shown in plan view in FIG. 2 and in side sectional view in FIG. 3. The lens of the present invention defines a central optical portion 24 of high optical quality. Central optical portion 24 preferably defines a bi-convex cross-section. Alternately, optical portion 24 may define a plano-convex cross section. The diameter of optical portion 24 is preferably about 5.8 mm. Extending on either side of optical portion 24 are tapered fixation elements 26. Fixation elements 26 are integrally formed with optical portion 24 by known techniques, such as computerized lathe cutting from a button of suitable material.

Figure 7:
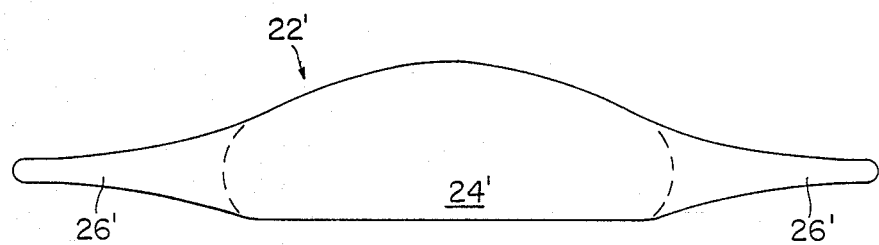
FIG. 7 is a side sectional view of a lens having plano-convex cross-section.

An optical portion defining a plano-convex cross-section is referred to above is shown in FIG. 7, 22' representing the lens, 24' representing the optical portion of the lens, and 26' representing fixation elements.

Lens 22 comprises an hydrogel material, i.e., a high optical quality, flexible, water absorbing material such as is known for soft contact lenses. According to a preferred embodiment, lens 22 comprises a hydrogel material having more than about 40% water content, most preferably having about 60% water content, such as Optimer 6½, manufactured and sold by T R Developement Ltd., England, or HEMA 60%. Hydrogel materials retain their firm consistency when fully expanded (i.e., fully hydrated), imitating natural physiological lenses, so they are better tolerated by the eye tissue than are hard lenses or soft silicone lenses. Hydrogel materials having about 60% water content are most preferred due to their index of refraction and other qualifies which are preferred for the eye due to lower glare phenomenon and less surface reflection. It will be appreciated that UV or other filters optionally may be added to the lenses as required.

As seen in FIG. 2 and 3, fixation elements 26 extend equidistantly on either side of optical portion 24 to permit centering of the lens within the eye. For example, a lens to be inserted into the lens capsule ("in the bag") of the eye of a mature adult, preferably has an optical portion 24 of about 5.8 mm in diameter, and fixation elements 26 each of about 2.4 to 2.7 mm in length. For a lens for fixation to the ciliary sulcus, the optical portion is also about 5.8 mm in diameter, while the fixation elements 26 will each be between about 3.1 and 4.1 mm in length. A lens for fixation in the anterior chamber angle has an optical portion of about 5.8 mm with fixation elements between about 2.3 mm to 3.8 mm. In lenses for children, the ratios will be about the same, though the overall length will be appropriately shorter, i.e., 10 mm. Apertures 30, which may comprise holes through the lens or merely indentations therein, are provided at the edges of the optical portion for engagement by a surgical instrument during insertion, such as for maneuvering the lens into position.

Figure 4:
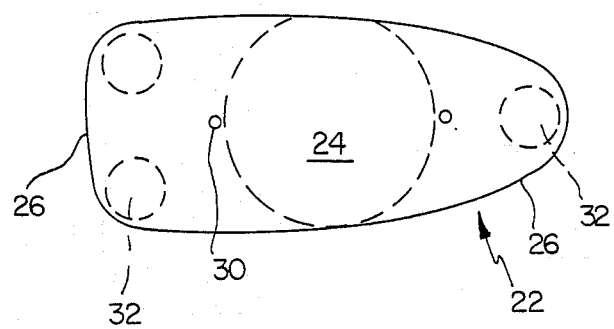
FIG. 4 is a plan view illustration of an intraocular lens constructed and operative in accordance with an alternate embodiment of the present invention.

It will be appreciated that the power of the inserted lens depends on the curvature and, thus, on the thickness of the optical portion. Preferably, the fixation elements will be about 0.2 to 0.3 mm thick at their ends, tapered gradually to that thickness from the optical portion. Thus, the optical portion of the lenses of the present invention can be formed with almost any desired curvature, the fixation elements being tapered accordingly, and most desired diopters can be provided. The lenses of the present invention are particularly suited for use as implant lenses of between 7 and 28 diopters. One example of suitable measurements for a lens according to the present invention is as follows:

length of lens (for insertion in the bag): 10.8 mm
    diameter of optical portion: 5.8 mm
    power of optical portion: 20 diopters
    thickness at center of bi-convex optical portion: 1.4 mm
    length of each fixation element: 2.5 mm
    thickness of fixation element at edge of optical portion: 0.7 mm
    thickness of fixation element at its outer end: 0.3 mm According to the embodiment illustrated in FIG. 2, the ends of the fixation elements are rectangular in shape with rounded corners. This permits fixation along much of the end surface of the fixation elements. Alternatively, as illustrated in FIG. 4, one of the fixation elements may be rectangular in shape while the other is tapered, as seen from above. This embodiment is useful because it permits insertion of the rectangular end first for rapid and effective fixation while leaving the tapered end exposed for subsequent insertion and manipulation as necessary to fit the lens over the iris and through the pupil into the posterior chamber. Alternatively, any other shape of fixation element can be utilized, provided that it is gradually tapered along its length (when seen in side section).

As can also be seen in FIG. 4, fenestration of the lens may be provided, i.e., a number of holes 32 may be provided in the fixation elements. These permit the lens capsule to join to itself through the holes when the capsule collapses about the lens and into engagement therewith, which increases the degree of fixation of the implanted lens in the eye.

It is a particular feature of the intraocular lens of the present invention that the lens is tapered from the edge of the optical portion all along the length of the fixation elements, as seen in side section. Thus, there is no weak point about which the lens can deform when dehydrated so as to interfere with insertion, as can occur with non-tapered hydrogel lenses.

The method of insertion of the lenses of the present invention will now be described with further reference to FIG. 1. A conventional incision is made through the limbus, whose length is determined by the particular method to be used to remove the natural lens and hard nucleus. A portion of the anterior lens capsule is removed (anterior capsulectomy) followed by expression of the nucleus. The incision is closed to about 3 to 6 mm, and water infused to the anterior chamber while suction is provided to suck out the cortex from the posterior chamber or phacoemulsification carried out.

The implant lens is dehydrated to the desired size for insertion, between 3 and 6 mm wide, and inserted through the incision towards the desired location. In some cases, such as insertion into the anterior chamber, the lens is not dehydrated at all, but inserted fully hydrated. For convenience of insertion into the posterior chamber, the lens can be dehydrated almost completely, i.e., to less than one half its hydrated length. As the lens enters the eye, it absorbs aqueous humor and begins to expand. Once the lens is in the desired orientation, i.e., past the iris and through the pupil into the posterior chamber, either in the bag or adjacent the ciliary sulcus, it completes its expansion.

It will be appreciated that, due to their relative thinness, the fixation elements hydrate faster than the optical portion, extending both in length and thickness. Thus, while complete hydration requires a longer period of time, hydration which occurs during the first five minutes after insertion is sufficient to prevent the lens implant from moving out of the desired location.

It is a particular feature of the intraocular lens of the present invention that the shape and material of which it is made permit dehydration of the lens to a size which is a fraction of the size of the lens when in use, i.e., 3 mm wide during insertion which expands to a width of 5.8 mm, which permits insertion through a relatively small incision without the necessity for folding the lens. Thus, the lens remains easily maneuverable and manipulable by the surgeon and the need for complicated unfolding maneuvers during insertion or within the eye is obviated.

Testing of the position within the eye when inserting the lens "in the bag" can be accomplished by engaging the lens at apertures 30 and moving the lens to one side. If the lens returns to the center by itself, it is properly located. If it remains to one side, it has not been inserted into the lens capsule, and can be further manipulated until it is properly located. The incision is then sutured, as in conventional eye surgery.

It will be appreciated by those skilled in the art that the invention is not limited to what has been shown and described hereinabove by way of example. Rather, the scope of the invention is limited solely by the claims which follow.

I claim:

1. An intraocular lens comprising a hydrogel material and defining:
    a central optical portion; and,
    only two oppositely disposed equidistant elongate, fixation elements integrally formed with and extending axially from said optical portion said fixation elements and optical portion defining a straight line, said fixation elements tapering gradually and symmetrically to a minimum along a smooth curve over its length to its outer end, said tapering being normal to the plane of said optical portion thereby substantially eliminating weak points at the interface between the optical portion and the fixation elements.

2. A lens according to claim 1 and wherein said hydrogel material comprises an optical quality hydrogel material having about 60% water content.

3. The lens of claim 1 wherein the lens gradually tapers symmetrically normal to the plane of the optical portion along its length from the optical portion to the outer ends of the fixation elements to a thickness of about 0.2–0.3 mm.

4. A lens according to claim 1, wherein said optical portion defines a bi-convex cross-section.

5. A lens according to claim 1, wherein said optical portion defines a plano-convex cross-section.

6. A lens according to claim 1, wherein at least one of said fixation elements is substantially rectangular at its end in the plane of the optical portion.

7. A lens according to claim 1, wherein one of said fixations elements defines a tapered end.

8. A method of operating in the eye comprising the steps of:
    removing the natural lens of the eye and part of the anterior capsule portion;
    dehydrating to the desired degree a lens implant of a hydrogel material defining a central optical portion and only two oppositely disposed, equidistant, elongate fixation elements integrally formed with said optical portion said fixation elements and optical portion defining a straight line, said fixation elements tapering gradually and symmetrically to a minimum along a smooth curve over its length to its outer end, said tapering being normal to the plane of said optical portion, thereby substantially eliminating weak points at the interface between the optical portion and fixation element;
    inserting said lens implant into the desired chamber of the eye; and,
    permitting the lens implant to expand into fixative contact in the desired location.

9. The method of claim 8 wherein said step of dehydrating to the desired degree comprises the step of dehydrating to the desired degree the lens to less than one-half of its hydrated length.

10. A method according to claim 8 wherein said step of dehydrating to the desired degree comprises the step of partially dehydrating the lens to about one half its fully hydrated size.

11. A method according to claim 8 wherein said step of inserting comprises the step of inserting the lens into the posterior lens capsule.

12. A method according to claim 8 wherein said step of inserting comprises the step of inserting the lens into the posterior chamber adjacent the ciliary body.

13. A method according to claim 8 wherein said step of inserting comprises the step of inserting the lens into the anterior chamber for fixation in the angle.

14. A method of operating in the eye comprising the steps of:
    removing the natural lens of the eye and part of the anterior capsule portion; and
    inserting into the desired chamber of the eye a lens implant comprising a hydrogel material wherein said lens implant is fully hydrated and defining a central optical portion; and only two oppositely disposed equidistant, elongate fixation elements integrally formed with and extending axially from said optical portion, said fixation elements and optical portion defining a straight line, said fixation elements tapering gradually and symmetrically to a minimum along a smooth curve over its length to its outer end, said tapering being normal to the plane of said optical portion, thereby substantially eliminating weak points at the interface between the optical portion and the fixation element.

* * * * *